(12) United States Patent
Gleason

(10) Patent No.: US 12,239,549 B2
(45) Date of Patent: Mar. 4, 2025

(54) TUBE TWISTER ENGAGING FILL TUBE

(71) Applicant: Spineology Inc., St. Paul, MN (US)

(72) Inventor: Joseph E. Gleason, Eagan, MN (US)

(73) Assignee: Spineology Inc., St. Paul, MN (US)

( * ) Notice: Subject to any disclaimer, the term of this patent is extended or adjusted under 35 U.S.C. 154(b) by 220 days.

(21) Appl. No.: 17/680,011

(22) Filed: Feb. 24, 2022

(65) Prior Publication Data

US 2022/0265439 A1    Aug. 25, 2022

Related U.S. Application Data

(60) Provisional application No. 63/153,159, filed on Feb. 24, 2021.

(51) Int. Cl.
*A61F 2/46* (2006.01)
*A61F 2/44* (2006.01)

(52) U.S. Cl.
CPC ............ *A61F 2/4601* (2013.01); *A61F 2/441* (2013.01)

(58) Field of Classification Search
CPC ........ A61F 2/46; A61F 2/4601; A61F 2/4611; A61F 2/441; A61J 1/1412; F16L 2201/10; B65D 2251/00; B65D 2251/04; B65D 83/04; A61B 1/00112
See application file for complete search history.

(56) References Cited

U.S. PATENT DOCUMENTS 10,231,846 B2 * 3/2019 Popejoy ............. A61B 17/8822

* cited by examiner

*Primary Examiner* — Si Ming Ku
(74) *Attorney, Agent, or Firm* — Skaar Ulbrich Macari, P.A.

(57) ABSTRACT

A surgical implant fill system can include a fill tube and a tube twister. A flange of the fill tube can be keyed to the tube twister so that the fill tube does not rotate independent from the tube twister when the flange is engaged with the tube twister. A release mechanism secures the flanged end to the tube twister. Visual and tactile indications can be provided on the tube twister to show the direction of the dispensing end of the fill tube.

15 Claims, 5 Drawing Sheets

TUBE TWISTER ENGAGING FILL TUBE

PRIORITY

This application claims the benefit of U.S. Provisional Application Ser. No. 63/153,159, filed on Feb. 24, 2021, which is hereby incorporated herein by reference in its entirety.

FIELD

The present invention generally relates to surgical instruments. More particularly, the present invention relates to instruments and methods for filling a surgical implant.

BACKGROUND

Fill tubes are used to fill implants for surgical procedures such as spinal fusion procedures. In the case of diverted fill tubes, there is a need for the surgeon to rotate the fill tube.

SUMMARY

The present invention is directed toward tools and methods of filling surgical implants, such as, for example, implants used for spinal surgical procedures.

A surgical implant fill system can include a fill tube and a tube twister. A flange of the fill tube can be keyed to the tube twister so that the fill tube does not rotate independent from the tube twister when the flange is engaged with the tube twister. A release mechanism secures the flanged end to the tube twister. Visual and tactile indications can be provided on the tube twister to show the direction of the dispensing end of the fill tube.

The fill tube can include an elongated hollow body having a distal dispensing end and an opposing proximal end, and a flange disposed at the proximal end that extends outward in a plane perpendicular to a longitudinal axis of the elongated hollow body. The tube twister can include a hub, including a recess defined therein, and a release lever provided to the hub. The release lever is movable between an open and a closed position with respect to the recess. The flange of the fill tube and the recess in the tube twister can be respectively sized and shaped such that the fill tube is keyed to the tube twister when the flange is disposed in the recess and the release lever is in the closed position.

A spring can be disposed in the tube twister such that the spring biases the release lever to the closed position. The flange can define a flat side and an opposing curved side. The tube twister can include tactile and/or visual indicators of the fill direction of the distal dispensing end of the fill tube. A dowel can be disposed in the tube twister such that the dowel guides the release lever as the release lever moves between the open and closed positions.

A surgical instrument can include a base, an inserter tube extending distally from the base, a handle extending radially from the base, a fill tube disposed longitudinally through the inserter tube, and a tube twister engaged with the proximal end of the fill tube. The flange and recess are respectively sized and shaped such that the fill tube is keyed to the tube twister when the flange is disposed in the recess and the release lever is in the closed position.

A method of operating a fill tube for filling a surgical implant can include keying a flanged end of a fill tube to a tube twister so that the fill tube cannot rotate axially relative to the tube twister. A release lever can be engaged with the flanged end so that the flanged end cannot be unkeyed when the release lever is in a closed position. The release lever can be biased to maintain the closed position. The tube twister can be rotated about a longitudinal axis of the fill tube to rotate a direction of a dispensing end of the fill tube. The direction of the dispensing end of the fill tube can be indicated visually and/or tactilely on the tube twister.

The release lever can be moved to an open position. Then the fill tube can be inserted through the tube twister in a distal direction while the release lever is in the open position until the flange engages a recess in the tube twister. The release lever can then be moved to the closed position. The movement of the release lever to the closed position can be automatically performed via a spring disposed in the tube twister.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
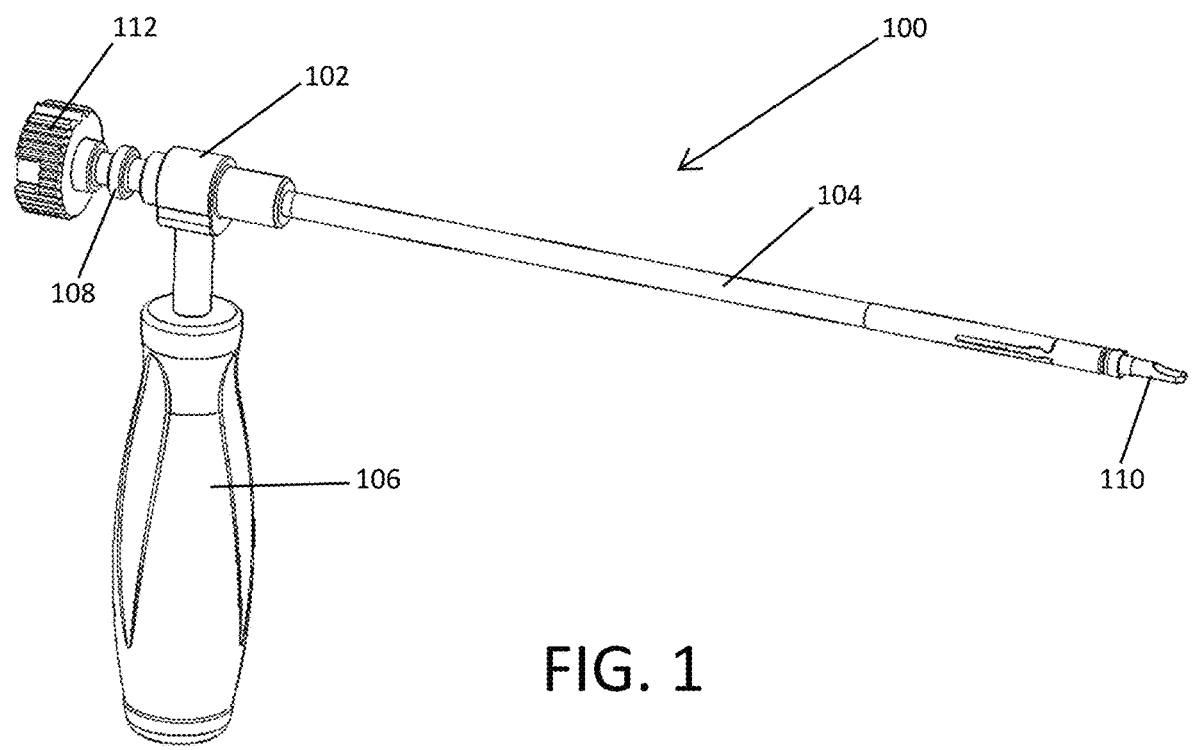
FIG. 1 is a perspective view of an implant filling instrument in accordance with embodiments of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention.

It should be appreciated that dimensional relationships among individual elements in the attached drawings are illustrated only for ease of understanding, but not to limit the actual scale.

The tube twister and the instrument system described herein allows a surgeon to rotate a diverted fill tube without first disengaging or partially withdrawing the fill tube. This allows the diverted fill tube to be rotated within a mesh implant during filling (bone stock discharged out of the fill tube) without first removing the fill tube from the compressed bone pack within the implant.

Referring to FIG. 1, an implant filling instrument 100 is shown. The instrument includes a base 102, an inserter tube 104 extending distally from the base 102, a handle 106 extending radially from the base 102, a fill end 108 disposed proximally of the base 102, a fill tube 110 disposed longitudinally through the inserter tube 104 from the fill end 108, and a tube twister 112 engaged with a proximal end of the fill tube 110.

Figure 2:
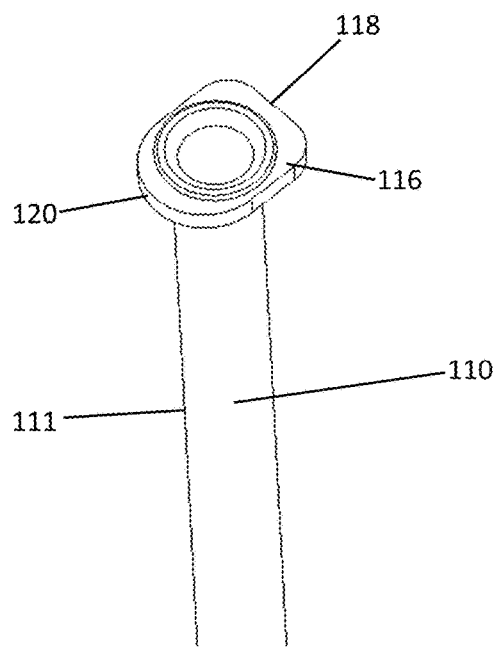
FIG. 2 is a perspective view of a proximal end of a fill tube in accordance with embodiments of the present invention.
Figure 3:
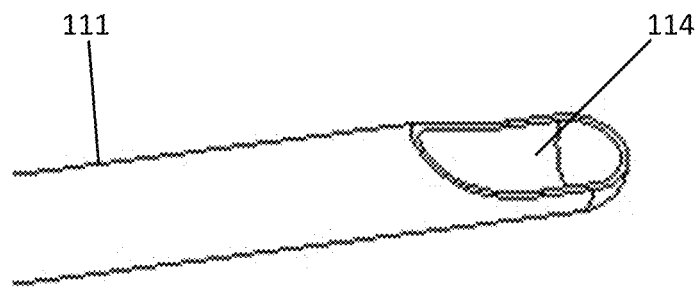
FIG. 3 is a perspective view of a distal end of a fill tube in accordance with embodiments of the present invention.
Figure 4:
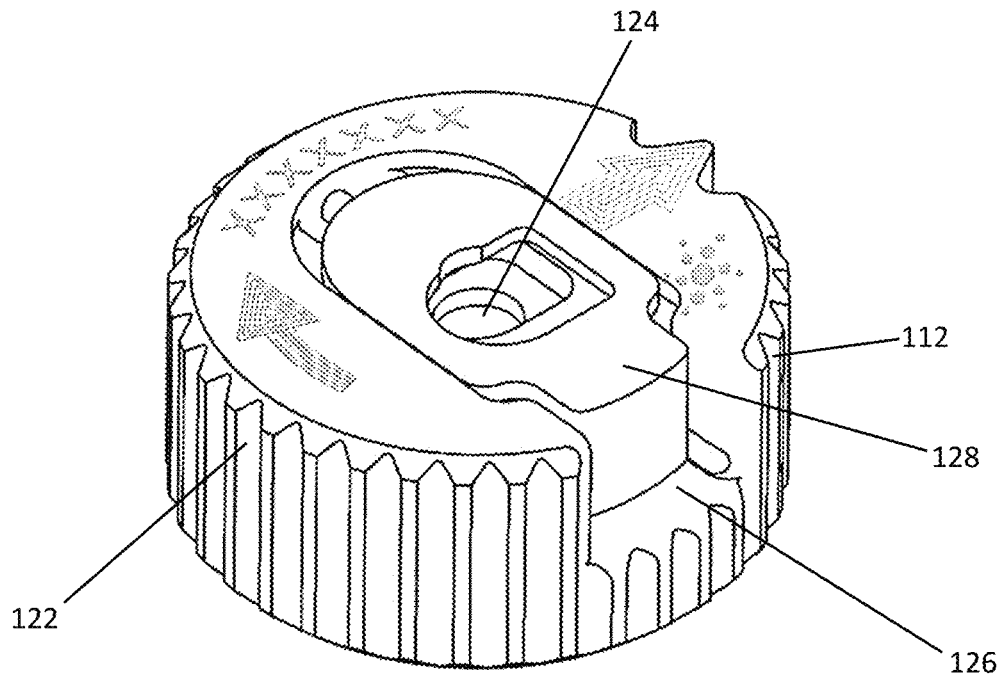
FIG. 4 is a perspective view of a fill tube twister in accordance with embodiments of the present invention.
Figure 5:
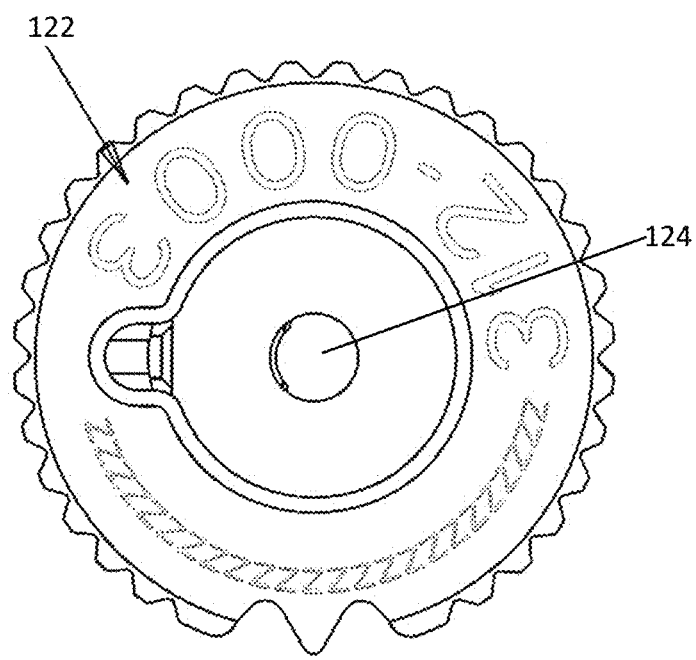
FIG. 5 is a bottom view of a fill tube twister in accordance with embodiments of the present invention.
Figure 6:
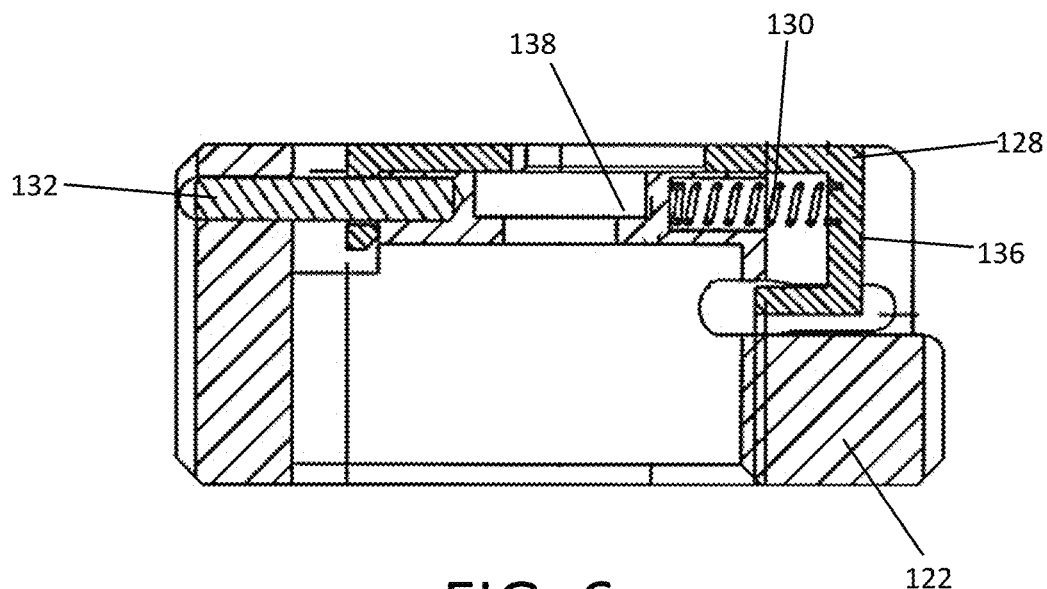
FIG. 6 is a side cross-sectional view of a fill tube twister in accordance with embodiments of the present invention.
Figure 7:
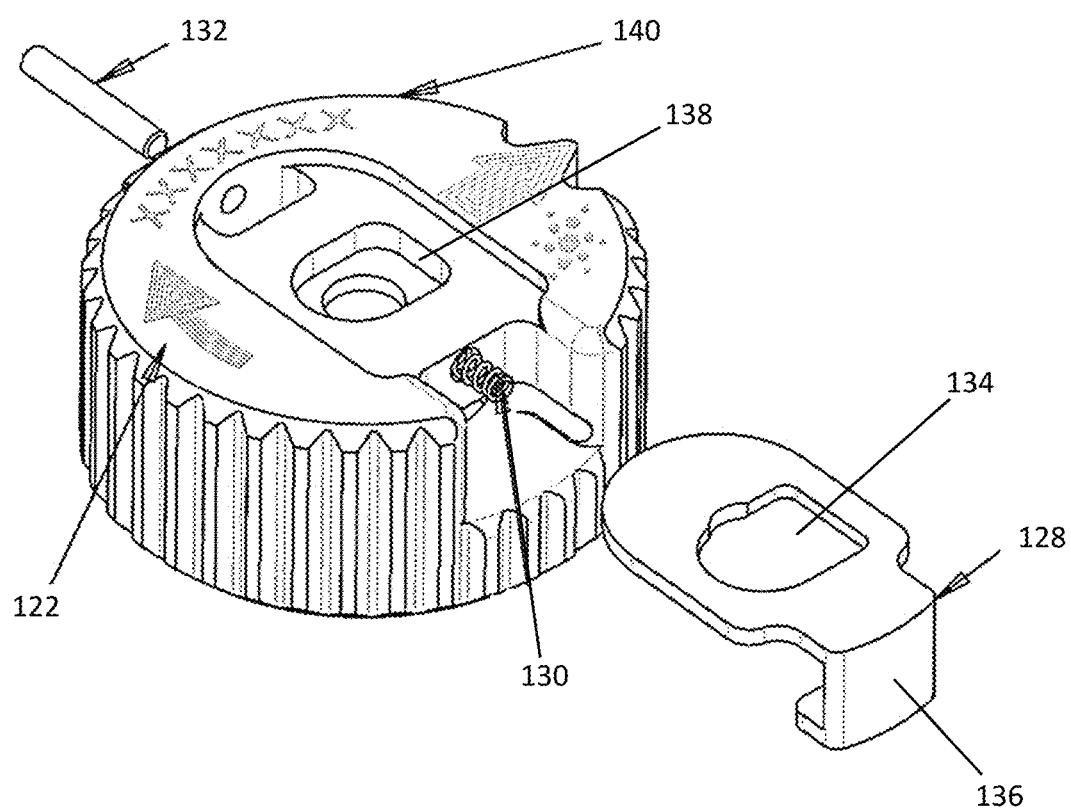
FIG. 7 is an exploded assembly perspective view of a fill tube twister in accordance with embodiments of the present invention.

As shown in FIGS. 1-3, the fill tube 110 is a diverter fill tube. An angled opening 114 is defined at a distal end of the elongated hollow body 111 of the fill tube 110. A flange 116 is formed at the proximal end of the elongated hollow body 111 of the fill tube 110. The flange 116 is eccentrically-shaped. In the depicted embodiment, the flange 116 extends in a plane perpendicular to the longitudinal axis of the fill tube's elongated hollow body, and defines a flat lateral side 118 and an opposing curved lateral side 120. In an end view along the longitudinal axis of the elongated hollow body 111 the flange 116 generally resembles a capital letter D.

Referring now to FIGS. 4-7, the tube twister 112 comprises a hub 122 that has a central aperture 124 defined therethrough in alignment with the longitudinal axis of the fill tube's 110 elongated hollow body. A lateral channel 126 is defined radially inward from a sidewall of the hub 122 to pass across the aperture 124. An engagement lever 128 (also referred to as a locking tab) is disposed in the channel such that the lever can translate radially inward and outward of the sidewall of the hub 122 in a plane perpendicular to the longitudinal axis of the fill tube's 110 elongated hollow body. A bias member, such as a spring 130, is disposed between a portion of the hub 122 and lever 128 to bias the lever 128 into a closed or engaged position as will be discussed below. A dowel 132 can be disposed in the hub 122 to support and guide the translating movement of the engagement lever 128 through its full travel.

The lever 128 defines an aperture 134 through its body such that the fill tube can pass entirely through the aperture, including the flange 116, as the fill tube 110 is inserted into the instrument 100 in the distal direction. A recess 138 is defined distally into a proximal-facing surface in the channel 126 of the hub 122. The recess 138 is sized and shaped to match the perimeter shape of the flange such that the fill tube 110 cannot rotate about its longitudinal axis when the flange 116 is seated in the recess 138. Thus, the fill tube 110 is keyed to the hub 122. The flange 116 is seated in the recess 138 when the fill tube 110 is fully disposed distally into the instrument 100. The outer circumferential surface 140 of the hub 122 can be textured or ribbed to provide enhanced grip by the surgeon.

Figure 8:
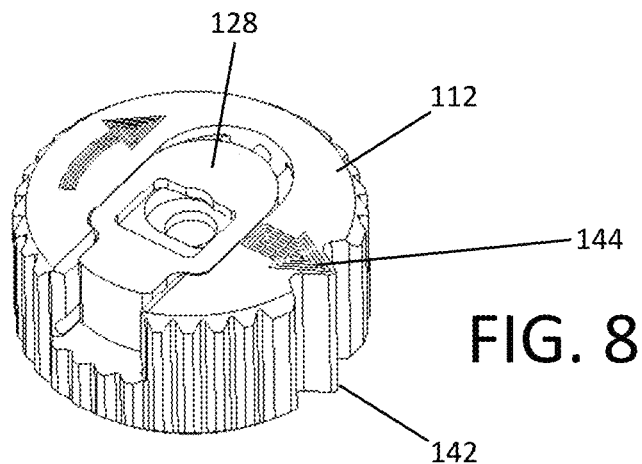
FIG. 8 is a perspective view of a fill tube twister in accordance with embodiments of the present invention.
Figure 9:
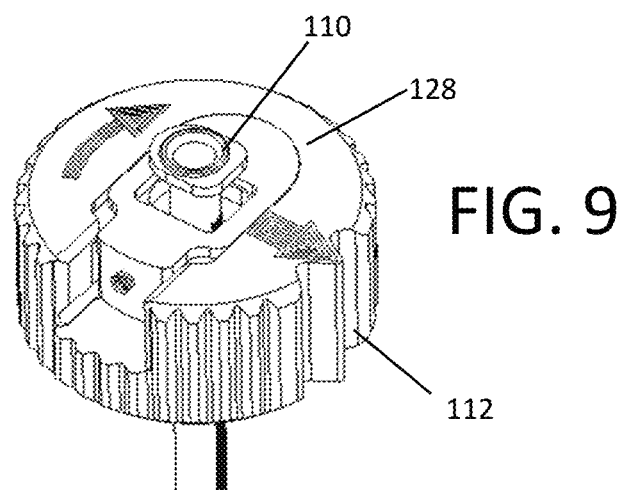
FIG. 9 is a perspective view of the fill tube twister of FIG. 8 engaging the proximal end of a fill tube in accordance with embodiments of the present invention.
Figure 10:
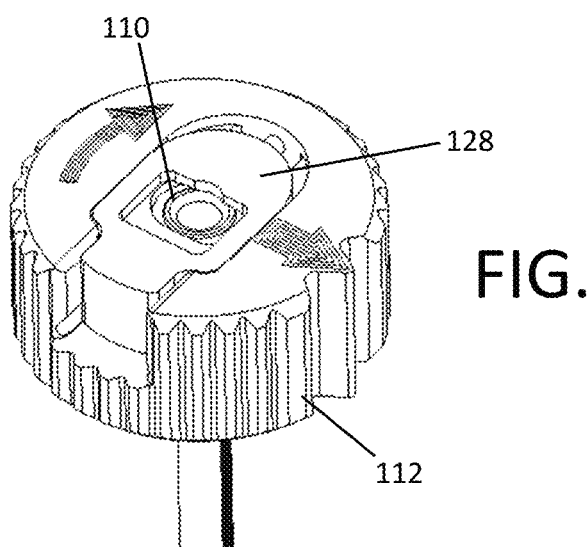
FIG. 10 is a perspective view of the fill tube twister of FIG. 8 disengaged from the proximal end of a fill tube in accordance with embodiments of the present invention.

Referring now to FIGS. 8-10, use or operation of the tube twister 112 will now be described. When the surgeon desires to rotate the orientation of the distal end of the fill tube 110, the tube twister 112 is rotated by grasping and rotating the hub 122. The distal end of the fill tube correspondingly rotates.

The tube twister 112 is shown in FIG. 8 prior to engaging the proximal end of the fill tube 110. The lever is biased into the closed or latched state until pressure is applied to the axially-exposed side 136 of the lever 128 by a finger or thumb of the operator (surgeon or other surgical personnel).

Moving now to FIG. 9, the lever 128 is being held in the release position by the operator (operator's thumb not shown) with sufficient force to overcome the force of the spring 130. The fill tube 110 is inserted into the instrument distal end first through the aperture 134 in the lever 128 and the center aperture 124 of the hub 122 until the flange 116 is seated in the recess 138 of the hub 122. Then the operator's force on the lever 128 is removed and the spring 130 causes the lever 128 to slide into the closed or latched position as shown in FIG. 10. It can be seen in FIG. 10 that the fill tube 110 cannot move proximally with respect to the tube twister 112 while the lever 128 is in the closed or latched position.

The surgeon can rotate the tube twister 112 to rotate the fill direction of the angled opening 114 of the fill tube 110.

Because the flange shape is keyed to the hub 122, the fill tube 110 is always seated in the same rotational position with respect to the hub 122. This allows rotational reference tactile marker 142 and/or visual marker 144 to be provided to indicate to the surgeon, both visually and tactilely, the fill direction of the angled opening 114.

The fill tube 110 can be removed from the tube twister 112 by reversing the steps described above.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A method of operating a fill tube for filling a surgical implant, the method comprising:
keying a flanged end of the fill tube to a tube twister so that the fill tube cannot rotate axially relative to the tube twister and so that the flanged end can only be keyed to the tube twister in one single axial orientation.

2. The method of claim 1, further comprising engaging a release lever with the flanged end so that the flanged end cannot be unkeyed when the release lever is in a closed position.

3. The method of claim 2, further comprising biasing the release lever to maintain the closed position.

4. The method of claim 2, further comprising:
moving the release lever to an open position;
inserting the fill tube through the tube twister in a distal direction while the release lever is in the open position until the flanged end engages a recess in the tube twister; and
moving the release lever to the closed position.

5. The method of claim 4, wherein the release lever is moved to the closed position automatically via a spring disposed in the tube twister.

6. The method of claim 1, further comprising rotating the tube twister about a longitudinal axis of the fill tube to rotate a direction of a dispensing end of the fill tube.

7. The method of claim 6, further comprising, indicating visually on the tube twister the direction of the dispensing end of the fill tube.

8. The method of claim 6, further comprising, indicating tactilely on the tube twister the direction of the dispensing end of the fill tube.

9. The method of claim 2, further comprising:
moving the release lever to an open position;
inserting the fill tube through the tube twister in a distal direction while the release lever is in the open position until the flanged end engages a recess in the tube twister; and
moving the release lever to the closed position.

10. The method of claim 9, wherein the release lever is moved to the closed position automatically via a spring disposed in the tube twister.

11. A method of operating a fill tube for filling a surgical implant, the method comprising:

keying a flanged end of the fill tube to a tube twister so that the fill tube cannot rotate axially relative to the tube twister; and
engaging a release lever with the flanged end by sliding the release lever in a direction transverse a rotational axis of the tube twister so that the flanged end of the fill tube cannot be unkeyed when the release lever is in a closed position.

12. The method of claim 11, further comprising biasing the release lever to maintain the closed position.

13. The method of claim 11, further comprising rotating the tube twister about a longitudinal axis of the fill tube to rotate a direction of a dispensing end of the fill tube.

14. The method of claim 13, further comprising, indicating visually on the tube twister the direction of the dispensing end of the fill tube.

15. The method of claim 13, further comprising, indicating tactilely on the tube twister the direction of the dispensing end of the fill tube.

* * * * *